US009622696B2

(12) United States Patent
He et al.

(10) Patent No.: US 9,622,696 B2
(45) Date of Patent: Apr. 18, 2017

(54) TEST DEVICE AND ROTATION MODULE THEREOF

(71) Applicants: LITE-ON ELECTRONICS (GUANGZHOU) LIMITED, Guangzhou OT (CN); Lite-On Technology Corporation, Taipei OT (TW)

(72) Inventors: Sz-Shian He, Taipei (TW); Chia-Chun Wei, Taipei (TW); Hung-Wei Chen, Taipei (TW); Wei-Chieh Hu, Taipei (TW)

(73) Assignees: LITE-ON ELECTRONICS (GUANGZHOU) LIMITED, Guangzhou (CN); Lite-On Technology Corporation, Taipei (TW)

( * ) Notice: Subject to any disclaimer, the term of this patent is extended or adjusted under 35 U.S.C. 154(b) by 203 days.

(21) Appl. No.: 14/306,244

(22) Filed: Jun. 17, 2014

(65) Prior Publication Data

US 2015/0305659 A1 Oct. 29, 2015

(30) Foreign Application Priority Data

Apr. 29, 2014 (CN) .......................... 2014 1 0177242

(51) Int. Cl.
*A61B 5/151* (2006.01)
*A61B 5/15* (2006.01)
*A61B 5/157* (2006.01)

(52) U.S. Cl.
CPC .......... *A61B 5/15163* (2013.01); *A61B 5/157* (2013.01); *A61B 5/150022* (2013.01); *A61B 5/15113* (2013.01); *A61B 5/15117* (2013.01); *A61B 5/15151* (2013.01); *A61B 5/150412* (2013.01); *A61B 5/150244* (2013.01)

(58) Field of Classification Search
CPC ........ A61B 5/150244; A61B 5/150916; A61B 5/15115; A61B 5/15132; A61B 5/15151; A61B 5/15163; A61B 5/15159
See application file for complete search history.

(56) References Cited

U.S. PATENT DOCUMENTS

2011/0130782 A1* 6/2011 Kan ..................... A61B 5/1411
606/182

* cited by examiner

*Primary Examiner* — Michael C Stout
(74) *Attorney, Agent, or Firm* — Jianq Chyun IP Office (57) ABSTRACT

A test device and a rotation module thereof are provided. The rotation module includes a rotation body and a driving element. The rotation body includes a shaft, a position limiting element, a reciprocation element, and a rotation element. The shaft is pivoted in a housing. The position limiting element and the reciprocation element are telescoped on the shaft, respectively. The rotation element engages with the shaft and is located between the position limiting element and the reciprocation element. The driving element is slideably disposed in the housing and coupled to a groove of the reciprocation element. When the driving element moves back and forth, the driving element drives the reciprocation element to rotate back and forth relative to the position limiting element through the groove. The rotation element is pushed by the reciprocation element to rotate along a rotation direction relative to the position limiting element.

15 Claims, 6 Drawing Sheets

TEST DEVICE AND ROTATION MODULE THEREOF

CROSS-REFERENCE TO RELATED APPLICATION

This application claims the priority benefit of China application serial no. 201410177242.8, filed on Apr. 29, 2014. The entirety of the above-mentioned patent application is hereby incorporated by reference herein and made a part of this specification.

BACKGROUND OF THE INVENTION

Field of the Invention

The invention relates to a test device, and more particularly, relates to a test device having a rotation module.

Description of Related Art

With development in technology and awareness in health issue, people pay more attentions each day to agendas such as health hygiene. Therefore, medical equipments have been constantly developed and improved in order to meet manufacturing standards of medical equipments as well as public demands.

Take a blood testing device as an example, in which many types of different blood-collecting devices have been derived, such as blood-collecting pen, lancets, blood-collecting tube and so on, so as to facilitate in simple blood testing. A test device is generally used together with single-use consumables. For example, the blood testing device on the market usually requires use of lancets and test sheets in bulk packing. Therein, the lancets and the test sheets belong to the single-use consumables which need to be thrown away once being used. According to current design of the test device, a user must manually install and remove the single-use consumables. For example, during the process in use, the user must manually install the lancets and the test sheets into the blood-collecting device. After a blood sample is obtained for testing, the user must again manually remove and throw away the lancets and the test sheets being used, and re-install the new lancets and the new test sheets the next time.

By doing so, although misgivings for bacterial infection or cross infection due to the consumables being repeatedly used by the user may be avoided, installing steps for the lancets and the test sheets are quite complicated to cause inconvenience for the user in use. Accordingly, it has became one of may important problems to be solved as how to improve the test device so it is able to automatically replace the consumables (e.g., the lancets and the test sheets) in the test device thereby improving convenience for the user in use.

SUMMARY OF THE INVENTION

The invention provides a test device having a rotation module, in which a carrying cartridge is driven by a unidirectional rotation characteristic of the rotation module to accomplish a purpose of automatically changing consumables installed in the carrying cartridge, so as to facilitate in improving convenience for the user in use.

A rotation module proposed by the invention can be disposed in a housing of a test device. The rotation module includes a rotation body and a driving element. The rotation body includes a shaft, a position limiting element, a reciprocation element, and a rotation element. The shaft is pivoted in a housing. The position limiting element and the reciprocation element are telescoped on the shaft, wherein the reciprocation element has a groove. The rotation element engages with the shaft and is located between the position limiting element and the reciprocation element. The driving element is slideably disposed in the housing and coupled to the groove. When the driving element moves back and forth towards a first direction and an opposite direction of the first direction, the driving element driving the reciprocation element to rotate back and forth relative to the position limiting element through the groove, and the rotation element being pushed by the reciprocation element to rotate along a rotation direction relative to the position limiting element for driving the shaft to rotate along the rotation direction.

A test device proposed by the invention includes a housing, a rotation module, a carrying cartridge and a push rod. The rotation module is disposed in the housing, which includes a rotation body and a driving element. The rotation body includes a shaft, a position limiting element, a reciprocation element, and a rotation element. The shaft is pivoted in the housing. The position limiting element and the reciprocation element are telescoped on the shaft, wherein the reciprocation element has a groove. The rotation element engages with the shaft and is located between the position limiting element and the reciprocation element. The driving element is slideably disposed in the housing and coupled to the groove. The carrying cartridge is detachably disposed on the shaft, wherein the carrying cartridge has a plurality of perforated grooves. The push rod connects the driving element, and is aligned to any one of the perforated grooves. When the driving element moves back and forth towards a first direction and an opposite direction of the first direction, the driving element driving the reciprocation element to rotate back and forth relative to the position limiting element through the groove, and the rotation element being pushed by the reciprocation element to rotate along a rotation direction relative to the position limiting element for driving the shaft to rotate along the rotation direction. The carrying cartridge rotates along the rotation direction together with the shaft, and the push rod is aligned to a next one of the perforated grooves.

Another test device proposed by the invention includes a housing, a rotation body, a driving element, a carrying cartridge and a push rod. The rotation body includes a shaft, a position limiting element, a reciprocation element, and a rotation element. The shaft is pivoted in the housing. The position limiting element and the reciprocation element are telescoped on the shaft, wherein the reciprocation element has a groove and the position limiting element is non-rotatably disposed in the housing. The rotation element engages with the shaft. The rotation element engages with the reciprocation element through a first ratchet wheel structure. The rotation element engages with the position limiting element through a second ratchet wheel structure. Therein, the rotation element is limited to unidirectionally rotate by the first ratchet wheel structure and the second ratchet wheel structure. The driving element is slideably disposed in the housing and coupled to the groove. The carrying cartridge is detachably disposed on the shaft, wherein the carrying cartridge has a plurality of perforated grooves. The push rod connects the driving element. When the driving element moves back and forth towards a direction, the driving element drives the reciprocation element to move back and forth through the groove for driving the rotation element to unidirectionally rotate while driving the shaft and the carrying cartridge to unidirectionally rotate.

In an embodiment of the invention, the rotation element has a first engaging portion and a second engaging portion opposite to each other, the position limiting element has a third engaging portion, and the reciprocation element has a fourth engaging portion, wherein the first engaging portion of the rotation element engages with the fourth engaging portion of the reciprocation element, and the second engaging portion of the rotation element engages with the third engaging portion of the position limiting element.

In an embodiment of the invention, when the driving element moves towards the first direction, the fourth engaging portion of the reciprocation element pushes the first engaging portion of the rotation element for driving the rotation element to rotate along the rotation direction, and the second engaging portion of the rotation element slides relative to the third engaging portion of the position limiting element.

In an embodiment of the invention, the position limiting element is slideably disposed on the housing, and the rotation body further includes an elastic element. The elastic element is telescoped on the shaft. The elastic element leans against the housing and the position limiting element for providing a pre-stress to hold the engagement between the second engaging portion of the rotation element and the third engaging portion of the position limiting element.

In an embodiment of the invention, when the driving element moves towards the opposite direction of the first direction, the fourth engaging portion of the reciprocation element slides relative to the first engaging portion of the rotation element, and the third engaging portion of the position limiting element blocks the second engaging portion of the rotation element for limiting the rotation element from rotating along an opposite direction of the rotation direction.

In an embodiment of the invention, the first engaging portion of the rotation element includes at least one first elastic locking hook, and the second engaging portion of the rotation element includes at least one second elastic locking hook. The first engaging portion of the rotation element engages with the fourth engaging portion of the reciprocation element through the first elastic locking hook, and the second engaging portion of the rotation element engages with the third engaging portion of the position limiting element through the second elastic locking hook.

In an embodiment of the invention, the carrying cartridge includes a plurality of consumables slideably disposed in the perforated grooves. When the driving element moves towards a first direction, the driving element drives the push rod to move into the next one of the perforated grooves being aligned and moves the consumable inside the next one of perforated grooves out of the carrying cartridge.

Based on above, with disposition and operation of the rotation module and the carrying cartridge according to the invention, when the driving element moves back and forth towards the first direction and the second direction, the driving element may drive the reciprocation element to rotate back and forth relative to the position limiting element, and the rotation element is limited to unidirectionally rotate because of the ratchet wheel structure between the rotation element and the reciprocation element and the ratchet wheel structure between the rotation element and the position limiting element. Meanwhile, the shaft and the carrying cartridge engaging with the shaft may be driven by the rotation element to unidirectionally rotate, so that the push rod may be sequentially aligned to each of the perforated grooves on the carrying cartridge. As a result, when each time the user is operating the test device, the push rod may smoothly move into the perforated groove to push out the consumables which is unused, so as to accomplish the purpose of automatically changing the consumables while preventing the consumables (e.g., the lancets and the test sheets) from being repeatedly used by the user and thereby avoiding misgivings for bacterial infection or cross infection. On the other hand, when the consumables inside the carrying cartridge are used up, the user can remove the used carrying cartridge, and assemble a new carrying cartridge on the shaft for subsequent uses thereby improving convenience for the user in use.

To make the above features and advantages of the disclosure more comprehensible, several embodiments accompanied with drawings are described in detail as follows.

DESCRIPTION OF THE EMBODIMENTS

Figure 1:
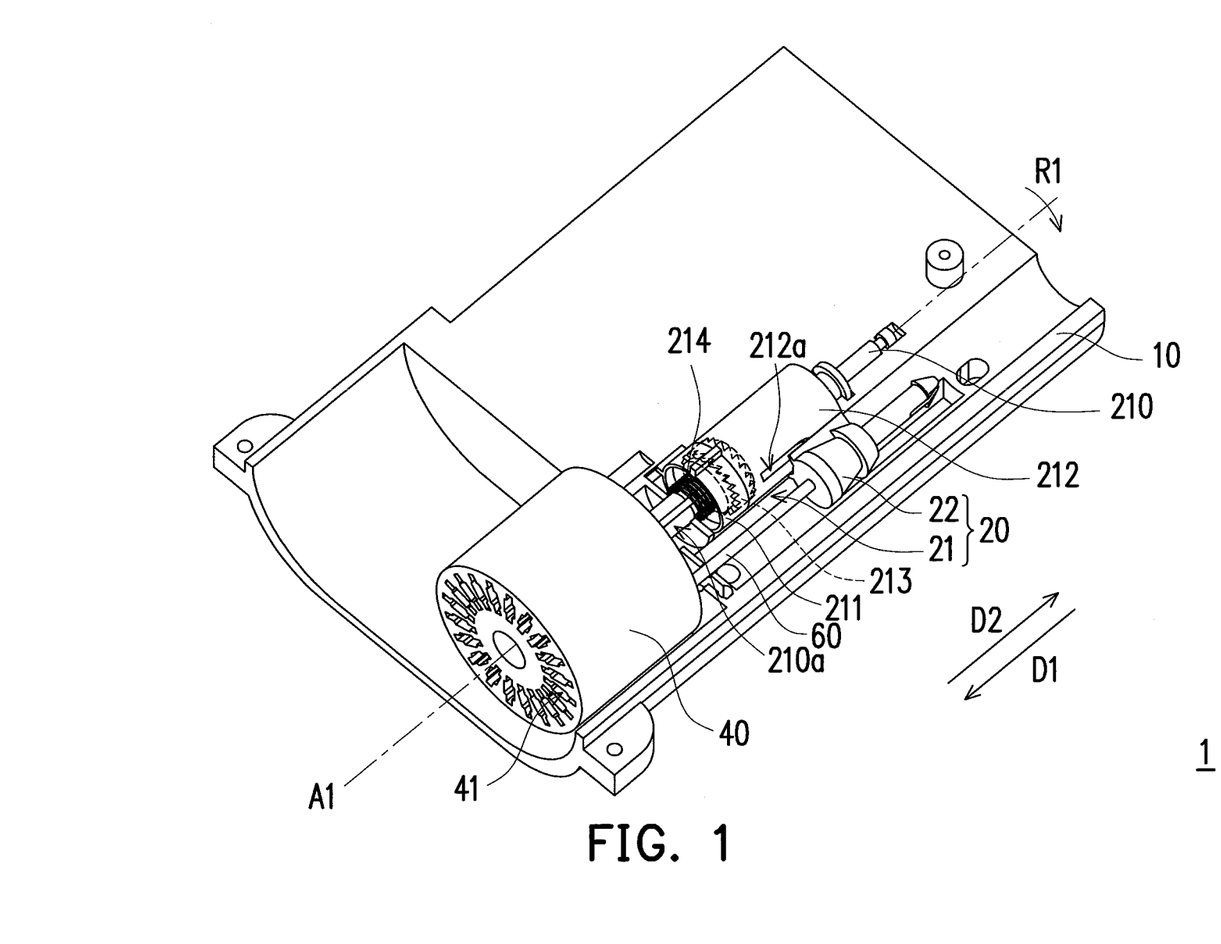
FIG. 1 is a schematic diagram of a test device according to an embodiment of the invention.
Figure 2:
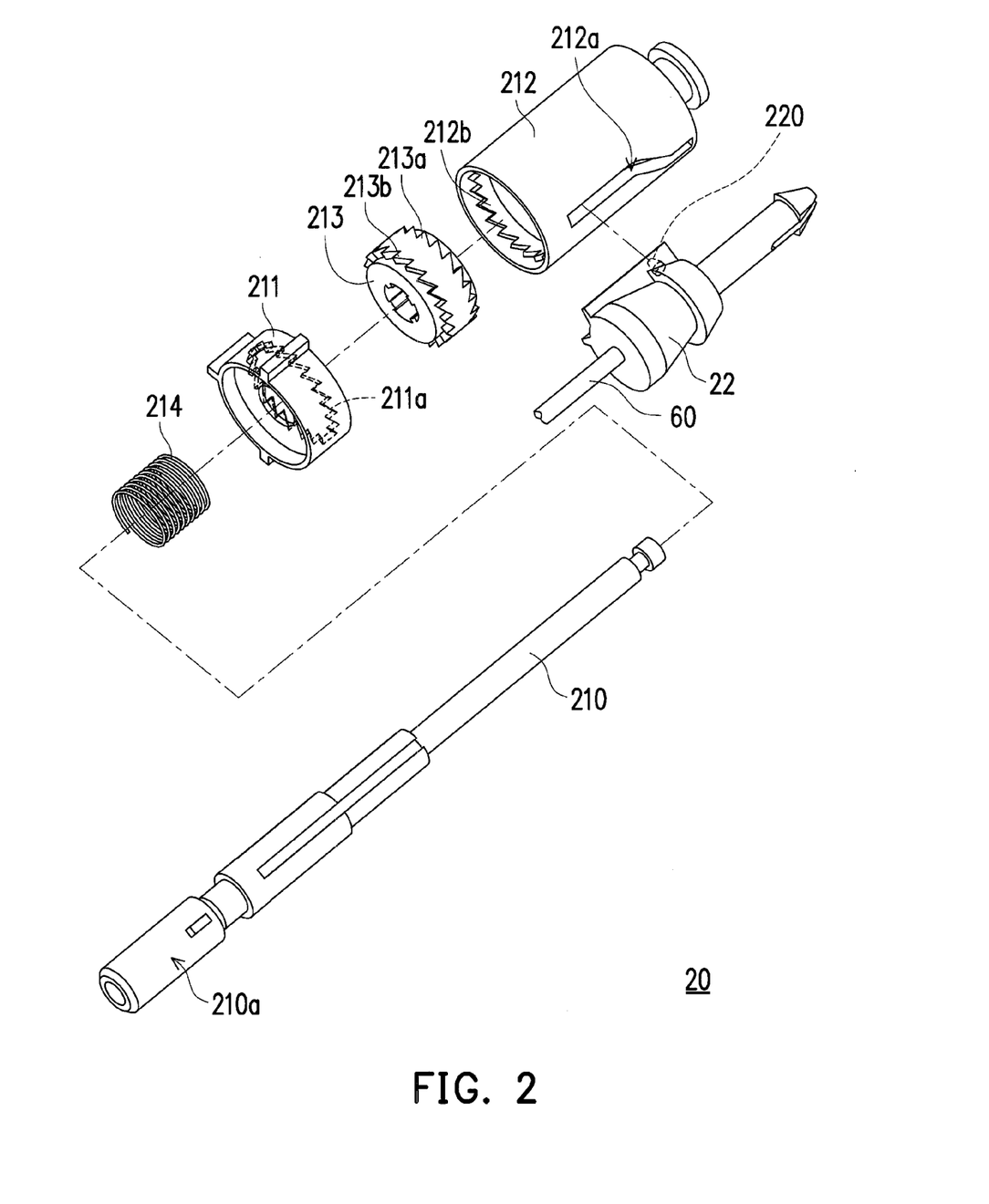
FIG. 2 is an explosion diagram of the rotation module depicted in FIG. 1.
Figure 3:
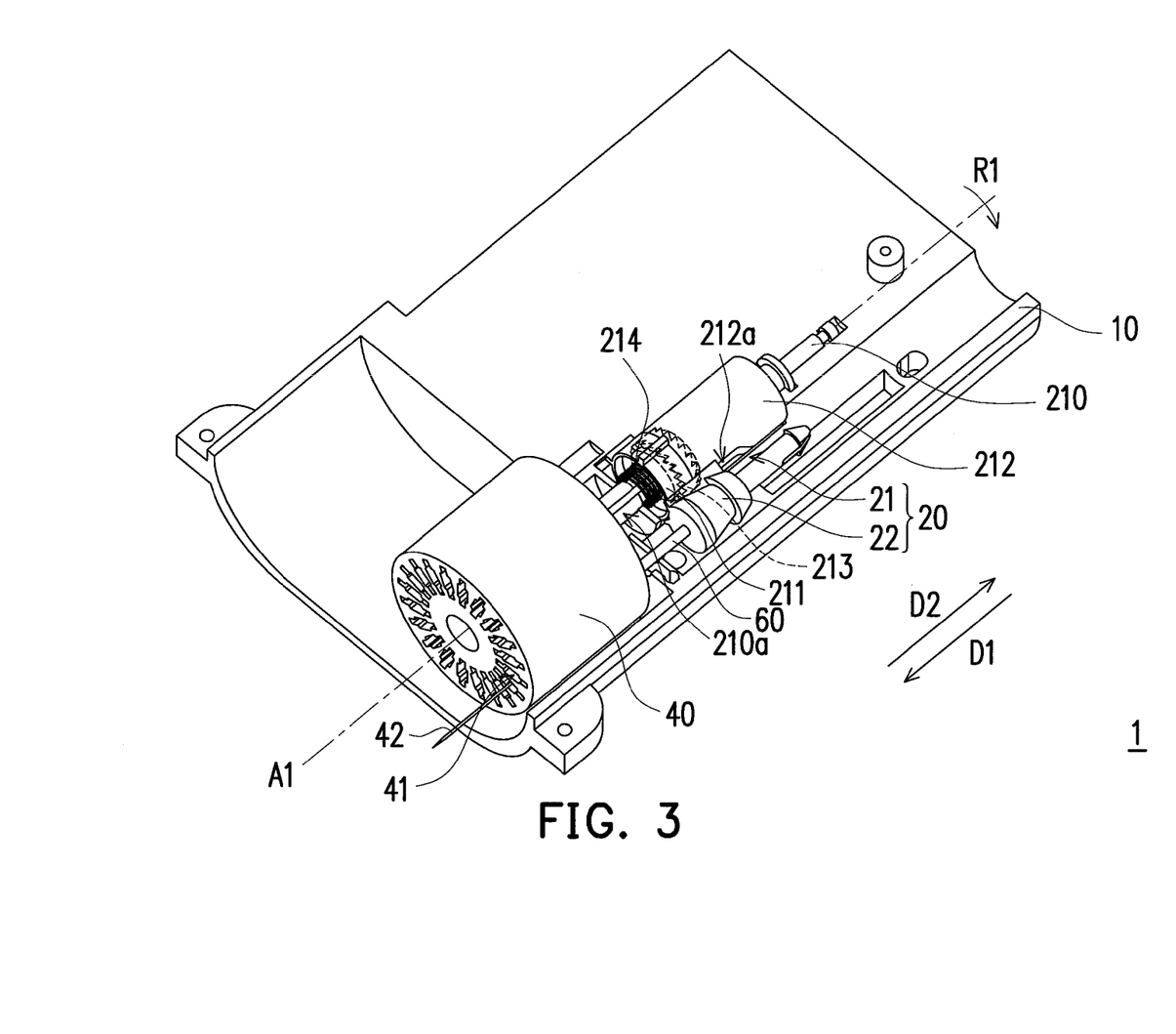
FIG. 3 is a schematic diagram after operating the test device of FIG. 1.

FIG. 1 is a schematic diagram of a test device according to an embodiment of the invention. FIG. 2 is an explosion diagram of the rotation module depicted in FIG. 1. FIG. 3 is a schematic diagram after operating the test device of FIG. 1. For clearer illustration and description, an upper portion of a housing 10 is omitted in FIG. 1 and FIG. 3. Referring to FIG. 1 to FIG. 3, in the present embodiment, a test device 1 includes the housing 10, a rotation module 20, a carrying cartridge 40 and a push rod 60, wherein the housing 10 may be composed of materials such as plastic, acrylic, metal, carbon fiber, a composite material thereof or other appropriate materials.

The rotation module 20 includes a rotation body 21 and a driving element 22; the rotation body 21 includes a shaft 210, a position limiting element 211, a reciprocation element 212 and a rotation element 213; and the shaft 210 is pivoted in the housing 10 along an axis A1. More specifically, the position limiting element 211 and the reciprocation element 212 may be sleeves or other similar members respectively telescoped on the shaft 210, and the rotation element 213 engages with the shaft 210, wherein the rotation element 213 is located between the position limiting element 211 and the reciprocation element 212. In the present embodiment, the position limiting element 211 may be movably but non-rotatably disposed in the housing 10. In other words, the position limiting element 211 can move on the shaft 210, whereas the rotation element 213 can drive the shaft 210 together to rotate relative to the position limiting element 211. Further, the reciprocation element 212 can rotate and move on the shaft 210. In the present embodiment, the driving element 22 is slideably disposed in the housing 10; the reciprocation element 212 has a groove 212a; and the driving element 22 is slideably coupled to the groove 212a.

For instance, the driving element 22 may include a guiding block 220, and the guiding block 220 is slideably disposed in the groove 212a.

As a detail structure of the rotation body 21, the rotation element 213 has a first engaging portion 213a and a second engaging portion 213b opposite to each other, whereas the position limiting element 211 has a third engaging portion 211a and the reciprocation element 212 has a fourth engaging portion 212b. More specifically, the first engaging portion 213 a of the rotation element 213 engages with the fourth engaging portion 212b of the reciprocation element 212, and the second engaging portion 213b of the rotation element 213 engages with the third engaging portion 211a of the position limiting element 211. Therein, the first engaging portion 213a and the fourth engaging portion 212b can be teeth pattern structures with complementary contour outlines for engaging with each other, and the second engaging portion 213b and the third engaging portion 211a can be teeth pattern structures with complementary contour outlines for engaging with each other. In the present embodiment, a pre-stress is applied among the three of the reciprocation element 212, the rotation element 213 and the position limiting element 211 so that they are in an engagement state.

In the present embodiment, an engagement between the rotation element 213 and the reciprocation element 212 is a first ratchet wheel structure, and the rotation element 213 has a first forward rotation direction relative to the reciprocation element 212. An engagement between the rotation element 213 and the position limiting element 211 is a second ratchet wheel structure, and the rotation element 213 has a second forward rotation direction relative to the position limiting element 211. Therein, rotation directions of the first forward rotation direction and the second forward rotation direction are identical. Taking FIG. 2 for example, the first ratchet wheel structure composed of engaging teeth between the rotation element 213 and the reciprocation element 212 makes the rotation element 213 to include the first forward rotation direction relative to the reciprocation element 212, wherein the first forward rotation direction is a rotation direction R1. Similarly, the second ratchet wheel structure composed of engaging teeth between the rotation element 213 and the position limiting element 211 makes the rotation element 213 to include the second forward rotation direction relative to the position limiting element 211, and the second forward rotation direction is the rotation direction R1.

Further more, in the present embodiment, because the position limiting element 211 is non-rotatably disposed in the housing 10, the rotation element 213 cannot rotate towards an opposite direction of the second forward rotation direction due to limitation by design of the second ratchet wheel structure between the rotation element 213 and the position limiting element 211.

In the present embodiment, the carrying cartridge 40 is detachably disposed on an end portion 210a of the shaft 210. More specifically, the carrying cartridge 40 includes a plurality of perforated grooves 41 arranged around the axis A1, wherein the carrying cartridge 40 may include a plurality of consumables 42 slideably disposed in the perforated grooves 41. In FIG. 3, the consumables 42 are illustrated as lancets 42 for example, but the invention is not limited thereto. The consumables may also be test sheets for testing. In the present embodiment, the push rod 60 connects the driving element 22, and when the driving element 22 moves in the housing 10, the driving element 22 can drive the push rod 60 to move together. Further, when the test device 1 is not operating, namely, before the lancet 42 inside the carrying cartridge 40 is pushed out of the carrying cartridge 40, the push rod 60 is aligned to any one of the perforated grooves 41.

In the present embodiment, the rotation element 213 in the rotation body 21 is driven to generate a step rotation through one back and forth movement of the driving element 22, so as to drive the carrying cartridge 40 to perform a rotation course, so that the push rod 60 is aligned to a next one of the perforated grooves 41. Further, during the back and forth movement of the driving element 22, the driving element 22 also drives the push rod 60 to move together to complete one stroke for the push rod 60, so as to push the consumables 42 inside the carrying cartridge 40 out of the carrying cartridge 40. Actuation processes and corresponding relationship between each element in the present embodiment are further described in detail as follows.

When the driving element 22 moves towards a first direction D1, the driving element 22 drives the reciprocation element 212 to rotate relative to the position limiting element 211 along the rotation direction R1 through the groove 212a, and the rotation element 213 is pushed by the reciprocation element 212 to rotate along the rotation direction R1 relative to the position limiting element 211 for driving the shaft 210 to rotate along the rotation direction R1. At the time, the carrying cartridge 40 also rotates along the rotation direction R1 together with the shaft 210, so that the push rod 60 is aligned to the next one of the perforated grooves 41 which is adjacent to afore-said any one of the perforated grooves 41 and moved into the next one of the perforated grooves 41, and thereby pushing the lancet 42 inside the next one of the perforated grooves 41 out of the carrying cartridge 40 for the user to perform subsequent testing operations.

In the present embodiment, through design of the first ratchet wheel structure and the second ratchet wheel structure at two opposite sides of the rotation element 213, the rotation element 213 includes the first forward rotation direction and the second forward rotation direction respectively relative to the reciprocation element 212 and the position limiting element 211, wherein the first forward rotation direction and the second forward rotation direction are both the rotation direction R1. When the reciprocation element 212 is driven by the driving element 22 to rotate along the rotation direction R1, due to design of the first ratchet wheel structure between the reciprocation element 212 and the rotation element 213, the fourth engaging portion 212b of the reciprocation element 212 and the first engaging portion 212a of the rotation element 213 being mutual engaged are structurally interfered. Therefore, the fourth engaging portion 212b of the reciprocation element 212 may push the first engaging portion 213a of the rotation element 213 for driving the rotation element 213 to rotate along the rotation direction R1. Meanwhile, the shaft 210 and the carrying cartridge 40 engaging with the shaft 210 also rotates along the rotation direction R1 together with the rotation element 213, so that the push rod 60 is aligned to the next one of the perforated grooves 41. Next, as the driving element 22 continues to move towards the first direction D1 to a firing position depicted in FIG. 3, the push rod 60 can move into the next one of the perforated grooves 41, so as to push the lancet 42 inside the next one of the perforated grooves 41 out of the carrying cartridge 40.

Further, when the rotation element 213 is pushed by the reciprocation element 212 to rotate along the rotation direction R1 in the above process, due to design of the second ratchet wheel structure between the rotation element 213 and the position limiting element 211, the second engaging portion 213b of the rotation element 213 and the third engaging portion 211a of the position limiting element 211 being mutual engaged are not structurally interfered. Therefore, the second engaging portion 213b of the rotation element 213 can slide relative to the third engaging portion 211a of the position limiting element 211, so that the rotation element 213 individually rotates along the rotation direction R1 (the second forward rotation direction) relative to the position limiting element 211.

In the present embodiment, the rotation body 21 may further include an elastic element 214, wherein the elastic element 214 is telescoped on the shaft 210 and leans against the housing 10 and the position limiting element 211. Because the position limiting element 211 is slideably disposed on the housing 10, when the second engaging portion 213b of the rotation element 213 slides relative to the third engaging portion 211a of the position limiting element 211, the position limiting element 211 is pushed by the rotation element 213 to move towards the first direction D1, so that the elastic element 214 is compressed. Accordingly, during the process in which the second engaging portion 213b of the rotation element 213 slides relative to the third engaging portion 211a of the position limiting element 211, the engagement state between the second engaging portion 213b of the rotation element 213 and the third engaging portion 211a of the position limiting element 211 is first being released. Next, under rotation of the rotation element 213 and pushing of the elastic element 214, the second engaging portion 213b of the rotation element 213 and the third engaging portion 211a of the position limiting element 211 are again restored back to the engagement state.

On the other hand, during the process in which the driving element 22 moves from the firing position depicted in FIG. 3 towards a second direction D2, the driving element 22 can drive the reciprocation element 212 to rotate along the opposite direction of the rotation direction R1 relative to the position limiting element 211 through the groove 212a. Due to the limitation in which the position limiting element 211 cannot rotate and design of the second ratchet wheel structure between the rotation element 213 and the position limiting element 211, the third engaging portion 211a of the position limiting element 211 can block the second engaging portion 213b of the rotation element 213 for limiting the rotation element 213 from rotating along the opposite direction of the rotation direction R1 (the second forward rotation direction). Accordingly, when the reciprocation element 212 is driven by the driving element 22 to rotate along the opposite direction of the rotation direction R1, due to design of the first ratchet wheel structure between the reciprocation element 212 and the rotation element 213, the fourth engaging portion 212b of the reciprocation element 212 and the first engaging portion 213a of the rotation element 213 being mutual engaged are not structurally interfered. Therefore, the fourth engaging portion 212b of the reciprocation element 212 can slide relative to the first engaging portion 213a of the rotation element 213, so that the reciprocation element 212 individually rotates along the opposite direction of the rotation direction R1 relative to the rotation element 213 and the position limiting element 211.

In other words, during the process in which the driving element 22 moves along the second direction D2 and drives the reciprocation element 212 to rotate along the opposite direction of the rotation direction R1, the rotation element 213 and the shaft 210 are not rotated, namely, the carrying cartridge 40 is not rotated. Further, during the process in which the driving element 22 moves from the firing position depicted in FIG. 3 towards the second direction D2 to an initial position depicted in FIG. 1, the driving element 22 also drives the push rod 60 to move out of the next one of the perforated grooves 41 and restore back to the initial position.

In brief, with disposition and operation of the rotation module 20 and the carrying cartridge 40, when the driving element 22 moves back and forth towards the first direction D1 and the second direction D2, the driving element 22 can drive the reciprocation element 212 to rotate back and forth relative to the position limiting element 211, and the rotation element 213 is limited to unidirectionally rotate because of the ratchet wheel structure between the rotation element 213 and the reciprocation element 212 and the ratchet wheel structure between the rotation element 213 and the position limiting element 211. Meanwhile, the shaft 210 and the carrying cartridge 40 engaging with the shaft 210 can be driven by the rotation element 213 to unidirectionally rotate, so that the push rod 60 can be sequentially aligned to each of the perforated grooves 41 on the carrying cartridge 40. As a result, when each time the user is operating the test device 1, the push rod 60 can smoothly move into the perforated groove 41 to push out the consumables 42 which is unused, so as to accomplish the purpose of automatically changing the consumables 42 while preventing the consumables 42 from being repeatedly used by the user and thereby avoiding misgivings for bacterial infection or cross infection. On the other hand, when the consumables 42 inside the carrying cartridge 40 are used up, the user can remove the used carrying cartridge 40, and assemble a new carrying cartridge 40 on the end portion 210a of the shaft 210 for subsequent uses.

Figure 4:
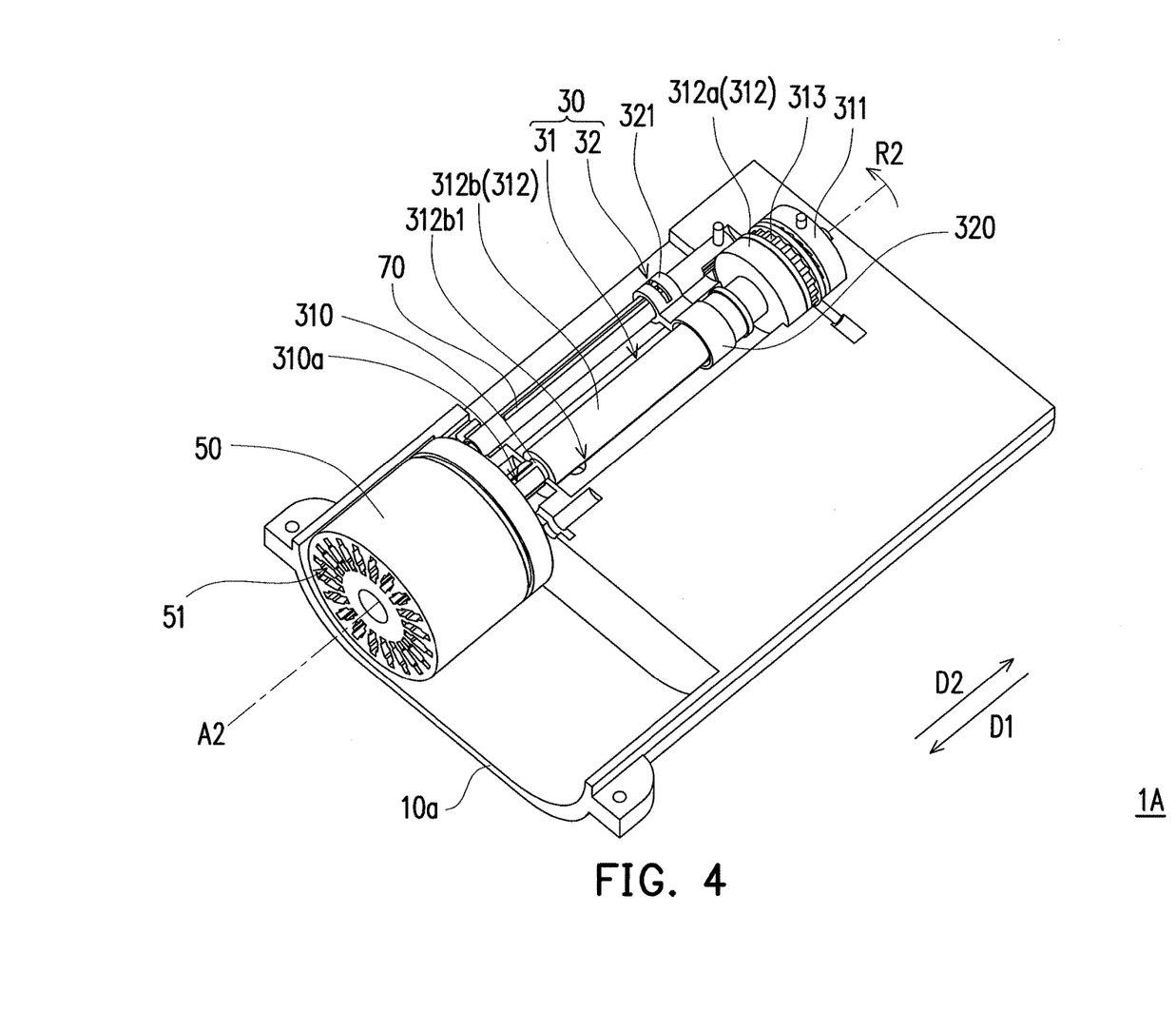
FIG. 4 is a schematic diagram of a test device according to another embodiment of the invention.
Figure 5:
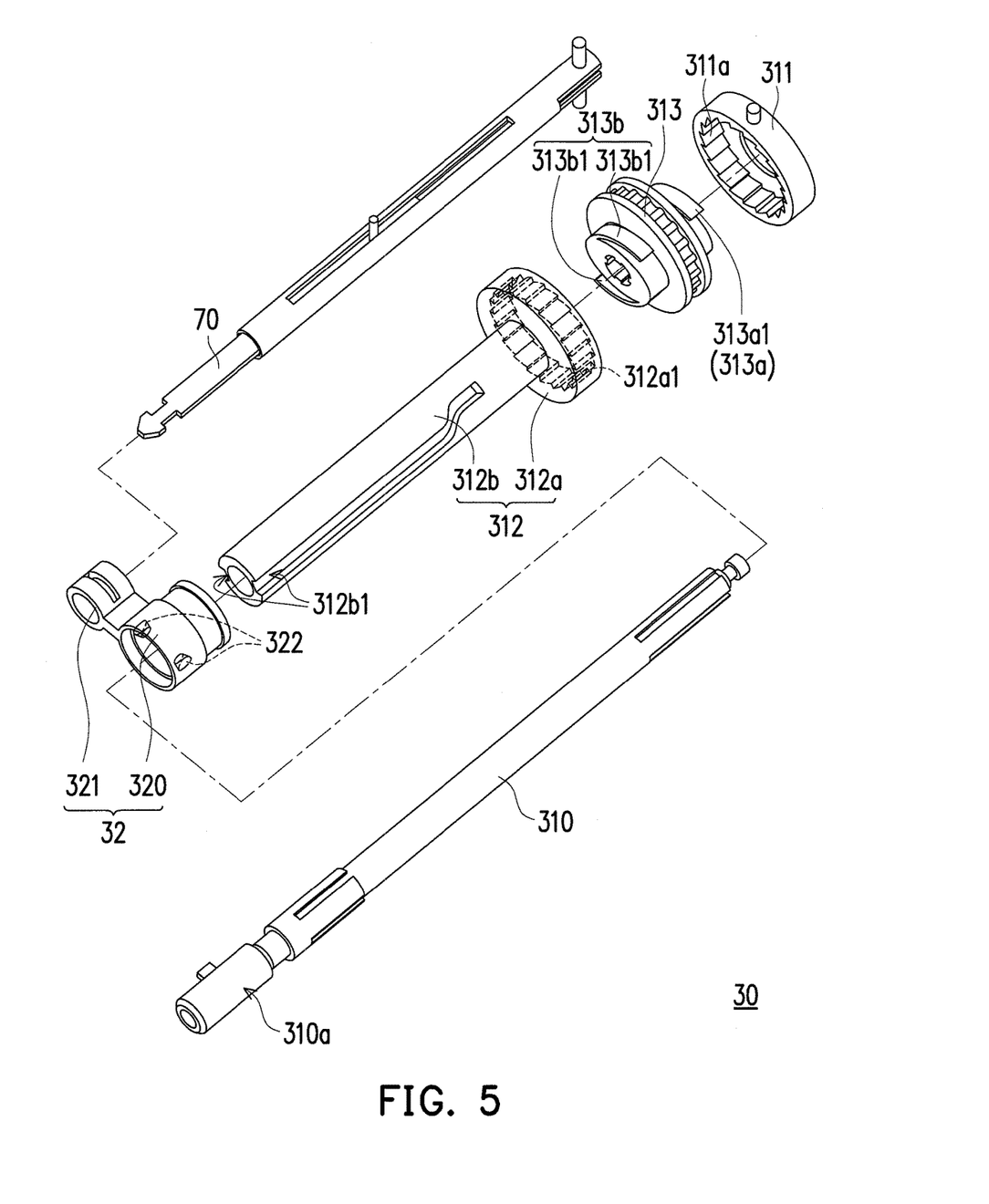
FIG. 5 is an explosion diagram of the rotation module depicted in FIG. 4.
Figure 6:
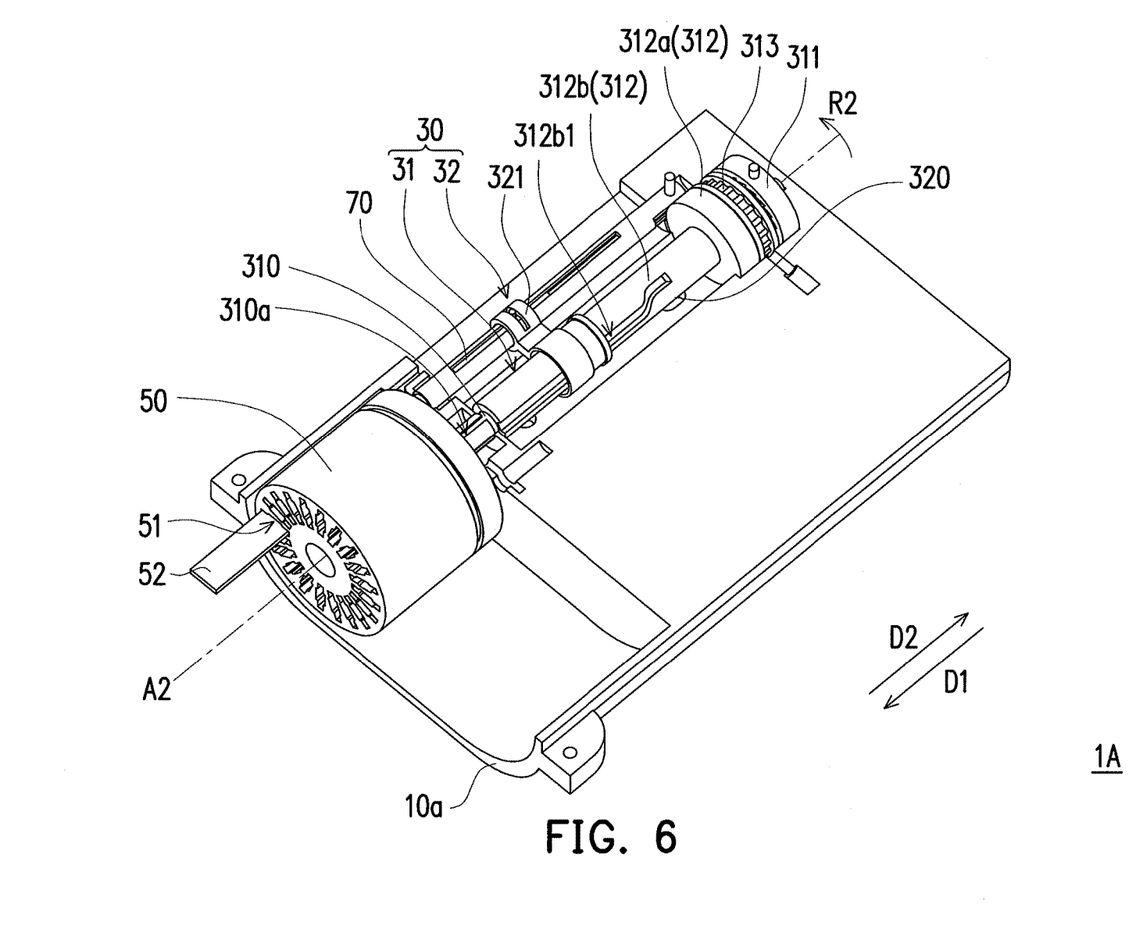
FIG. 6 is a schematic diagram after operating the test device of FIG. 4.

FIG. 4 is a schematic diagram of a test device according to another embodiment of the invention. FIG. 5 is an explosion diagram of the rotation module depicted in FIG. 4. FIG. 6 is a schematic diagram after operating the test device of FIG. 4. For clearer illustration and description, an upper portion of a housing 10a is omitted in FIG. 4 and FIG. 6. Referring to FIG. 4 to FIG. 6, in the present embodiment, a test device 1A includes the housing 10a, a rotation module 30, a carrying cartridge 50 and a push rod 70. The test device 1A of the present embodiment is substantially similar to the test device 1 of the foregoing embodiment, except that the rotation module 30 in the housing 10a is different from the rotation module 20 of the foregoing embodiment.

More specifically, the rotation module 30 includes a rotation body 31 and a driving element 32; the rotation body 31 includes a shaft 310, a reciprocation element 312, a position limiting element 311 and a rotation element 313; and the shaft 310 is pivoted in the housing 10a along an axis A2. More specifically, the position limiting element 311 and the reciprocation element 312 can be sleeves or other similar members respectively telescoped on the shaft 310, and the rotation element 313 engages with the shaft 310, wherein the rotation element 313 is located between the position limiting element 311 and the reciprocation element 312. In the present embodiment, the position limiting element 311 is non-rotatably disposed in the housing 10a. In other words, the rotation element 313 can drive the shaft 310 to rotate together relative to the position limiting element 311, whereas the reciprocation element 312 can rotate on the shaft 310. In the present embodiment, the reciprocation element 312 can include a first part 312a and a second part 312b connected to each other and a groove 312b1 disposed on the second part 312b. The driving element 32 is slideably disposed in the housing 10a, and the driving element 32 is slideably coupled to the groove 312b1.

The driving element 32 can include a first sleeve portion 320, a second sleeve portion 321 and a guiding block 322 disposed corresponding to the groove 312b1. The guiding block 322 is located on an inner peripheral surface of the first sleeve 320, and the guiding block 322 can be slideably coupled in the groove 312b1 after the first sleeve portion 320 of the driving element 32 is telescoped on the second part 312b of the reciprocation element 312. In this embodiment, two sets of the groove 312b1 and the guiding block 322 being correspondingly disposed are included. However, in other embodiments, a number of sets of the groove 312b1 and the guiding block 322 being correspondingly disposed can also be adjusted according to design requirements, which is not limited by the above disposition.

As a detail structure of the rotation body 31, the rotation element 313 has a first engaging portion 313a and a second engaging portion 313b opposite to each other, whereas the position limiting element 311 has a third engaging portion 311a and the reciprocation element 312 has a fourth engaging portion 312a1 disposed on the first part 312a. In the present embodiment, the first engaging portion 313a of the rotation element 313 includes at least one first elastic locking hook 313a1, and the second engaging portion 313b of the rotation element 313 includes at least one second elastic locking hook 313b1. More specifically, the first engaging portion 313a of the rotation element 313 engages with the third engaging portion 311a of the position limiting element 311 through the first elastic locking hook 313a1, and the second engaging portion 313b of the rotation element 313 engages with the fourth engaging portion 312a1 of the reciprocation element 312 through the second elastic locking hook 313b1. Herein, it is illustrated by using two first elastic locking hooks 313a1 and two second elastic locking hook 313b1 for example, but the invention is not limited thereto. In other embodiments, a number of the first elastic locking hook 313a1 and a number of the second elastic locking hook 313b1 can also be adjusted according to design requirements.

In the present embodiment, an engagement between the rotation element 313 and the reciprocation element 312 is a first ratchet wheel structure, and the rotation element 313 has a first forward rotation direction relative to the reciprocation element 312. The engagement between the rotation element 313 and the position limiting element 311 is the second ratchet wheel structure, which makes the rotation element 313 to include a second forward rotation direction relative to the position limiting element 311, wherein rotation directions of the first forward rotation direction and the second forward rotation direction are identical. Taking FIG. 5 for example, the first ratchet wheel structure composed of engaging teeth between the rotation element 313 and the reciprocation element 312 makes the rotation element 313 to include the first forward rotation direction relative to the reciprocation element 312, and the first forward rotation direction is a rotation direction R2. Similarly, the second ratchet wheel structure composed of engaging teeth between the rotation element 313 and the position limiting element 311 makes the rotation element 313 to include the second forward rotation direction relative to the position limiting element 311, and the second forward rotation direction is the rotation direction R2.

Further, in the present embodiment, the position limiting element 311 is non-rotatably disposed in the housing 10a. Accordingly, the rotation element 313 cannot rotate towards an opposite direction of the second forward rotation direction due to limitation by design of the second ratchet wheel structure between the rotation element 313 and the position limiting element 311.

In the present embodiment, the carrying cartridge 50 is detachably disposed on an end portion 310a of the shaft 310. More specifically, the carrying cartridge 50 includes a plurality of perforated grooves 51 arranged around the axis A2, wherein the carrying cartridge 50 can include a plurality of consumables 52 slideably disposed in the perforated grooves 51. In FIG. 6, the consumables 52 are illustrated as test sheets 52 for testing for example, but the invention is not limited thereto. The consumables can also be lancets. In the present embodiment, the push rod 70 connects the second sleeve portion 321 of the driving element 32, and when the driving element 32 moves in the housing 10a, the driving element 32 can drive the push rod 70 to move together. Further, when the test device 1A is not operating, namely, before the test sheet 52 inside the carrying cartridge 50 is pushed out of the carrying cartridge 50, the push rod 70 is aligned to any one of the perforated grooves 51.

In the present embodiment, the rotation element 313 in the rotation body 31 is driven to generate a step rotation through one back and forth movement of the driving element 32, so as to drive the carrying cartridge 50 to perform a rotation course, so that the push rod 70 is aligned to a next one of the perforated grooves 51. Further, during the back and forth movement of the driving element 32, the driving element 32 also drives the push rod 70 to move together to complete one stroke for the push rod 70, so as to push the consumables 52 inside the carrying cartridge 50 out of the carrying cartridge 50. Actuation processes and corresponding relationship between each element in the present embodiment are further described in detail as follows.

When the driving element 32 moves towards the first direction D1, the driving element 32 can drive the reciprocation element 312 to rotate along the rotation direction R2 relative to the position limiting element 311 through the groove 312b1, and the rotation element 313 is pushed by the reciprocation element 312 to rotate along the rotation direction R2 relative to the position limiting element 311, so as to drive the shaft 310 to rotate along the rotation direction R2. At the time, the carrying cartridge 50 also rotates along the rotation direction R2 together with the shaft 310, so that the push rod 70 is aligned to the next one of the perforated grooves 51 which is adjacent to afore-said any one of the perforated grooves 51 and moved into the next one of the perforated grooves 51, and thereby pushing the test sheet 52 inside the next one of the perforated grooves 51 out of the carrying cartridge 50 for the user to perform subsequent detection operations.

In the present embodiment, through design of the first ratchet wheel structure and the second ratchet wheel structure at two opposite sides of the rotation element 313, the rotation element 313 includes the first forward rotation direction and the second forward rotation direction respectively relative to the reciprocation element 312 and the position limiting element 311, wherein the first forward rotation direction and the second forward rotation direction are both the rotation direction R2. When the reciprocation element 312 is driven by the driving element 32 to rotate along the rotation direction R2, due to design of the first ratchet wheel structure between the reciprocation element 312 and the rotation element 313, the fourth engaging portion 312a1 of the reciprocation element 312 and the second elastic locking hook 313b1 of the second engaging portion 313b of the rotation element 313 are structurally interfered. Therefore, the fourth engaging portion 312a1 of the reciprocation element 312 can push the second elastic locking hook 313b1 of the second engaging portion 313b of the rotation element 313 for driving the rotation element 313 to rotate along the rotation direction R2. Meanwhile, the shaft 310 and the carrying cartridge 50 engaging with the shaft 310 also rotates along the rotation direction R2 together with the rotation element 313, so that the push rod 70 is aligned to the next one of the perforated grooves 51. Next, as the driving element 32 continues to move towards the first direction D1 to a firing position depicted in FIG. 6, the push rod 70 can move into the next one of the perforated grooves 51, so as to push the test sheet 52 inside the next one of the perforated grooves 51 out of the carrying cartridge 50.

Further, when the rotation element 313 is pushed by the reciprocation element 312 to rotate along the rotation direction R2 in the above process, due to design of the second ratchet wheel structure between the rotation element 313 and the position limiting element 311, the first engaging portion 313a of the rotation element 313 and the third engaging portion 311a of the position limiting element 311 are not structurally interfered. Therefore, the first elastic locking hook 313a1 of the first engaging portion 313a of the rotation element 313 can slide relative to the third engaging portion 311a of the position limiting element 311, so that the rotation element 313 individually rotates along the rotation direction R2 (the second forward rotation direction) relative to the position limiting element 311.

On the other hand, during the process in which the driving element 32 moves from the firing position depicted in FIG. 6 towards a second direction D2, the driving element 32 can drive the reciprocation element 312 to rotate along the opposite direction of the rotation direction R2 relative to the position limiting element 311 through the groove 312b1. Due to the limitation in which the position limiting element 311 cannot rotate and design of the second ratchet wheel structure between the rotation element 313 and the position limiting element 311, the third engaging portion 311a of the position limiting element 311 can block the first elastic locking hook 313a1 of the first engaging portion 313a of the rotation element 313 for limiting the rotation element 313 from rotating along the opposite direction of the rotation direction R2 (the second forward rotation direction). Accordingly, when the reciprocation element 312 is driven by the driving element 32 to rotate along the opposite direction of the rotation direction R2, due to design of the first ratchet wheel structure between the reciprocation element 312 and the rotation element 313, the fourth engaging portion 312a1 of the reciprocation element 312 and the second elastic locking hook 313b1 of the second engaging portion 313b of the rotation element 313 are not structurally interfered. Therefore, the fourth engaging portion 312a1 of the reciprocation element 312 can slide relative to the second elastic locking hook 313b1 of the second engaging portion 313b of the rotation element 313, so that the reciprocation element 312 individually rotates along the opposite direction of the rotation direction R2 relative to the rotation element 313 and the position limiting element 311.

In other words, during the process in which the driving element 32 moves along the second direction D2 and drives the reciprocation element 312 to rotate along the opposite direction of the rotation direction R2, the rotation element 313 and the shaft 310 are not rotated, namely, the carrying cartridge 50 is not rotated. Further, during the process in which the driving element 32 moves from the firing position depicted in FIG. 6 towards the second direction D2 to an initial position depicted in FIG. 4, the driving element 32 also drives the push rod 70 to move out of the next one of the perforated grooves 51 and restore back to the initial position.

In brief, with disposition and operation of the rotation module 30 and the carrying cartridge 50, when the driving element 32 moves back and forth towards the first direction D1 and the second direction D2, the driving element 32 can drive the reciprocation element 312 to rotate back and forth relative to the position limiting element 311, and the rotation element 313 is limited to unidirectionally rotate because of the ratchet wheel structure between the rotation element 313 and the reciprocation element 312 and the ratchet wheel structure between the rotation element 313 and the position limiting element 311. Meanwhile, the shaft 310 and the carrying cartridge 50 engaging with the shaft 310 can be driven by the rotation element 313 to unidirectionally rotate, so that the push rod 70 can be sequentially aligned to each of the perforated grooves 51 on the carrying cartridge 50.

As a result, when each time the user is operating the test device 1A, the push rod 70 can smoothly move into the perforated groove 51 to push out the consumables 52 which is unused, so as to accomplish the purpose of automatically changing the consumables 52 while preventing the consumables 52 from being repeatedly used by the user and thereby avoiding misgivings for bacterial infection or cross infection. On the other hand, when the consumables 52 inside the carrying cartridge 50 are used up, the user can remove the used carrying cartridge 50, and assemble a new carrying cartridge 50 on the end portion 310a of the shaft 310 for subsequent uses.

In summary, the rotation module proposed by the invention is capable of limiting the rotation element in unidirectional rotation through the ratchet wheel structure between the rotation element and the reciprocation element and the ratchet wheel structure between the rotation element and the reciprocation element, so as to drive the carrying cartridge to unidirectionally rotate. Further, the rotation module proposed by the invention is also capable of driving the reciprocation element to generate the back and forth movement through the back and forth movement of the driving element, so that the rotation element can unidirectionally rotate. The invention provides embodiments for two different designs for the ratchet wheel structure, but the invention is not limited thereto. The ratchet wheel structure proposed by the invention is configured to make the rotation element to include the same forward rotation direction relative to both the reciprocation element and the position limiting element.

With disposition and operation of the rotation module and the carrying cartridge, when each time the user is operating the test device, the push rod can smoothly move into the perforated groove to push out the consumables (e.g., the lancets and the test sheets) which is unused, so as to accomplish the purpose of automatically changing the consumables while preventing the consumables from being repeatedly used by the user and thereby avoiding misgivings for bacterial infection or cross infection. On the other hand, when the consumables inside the carrying cartridge are used up, the user can remove the used carrying cartridge, and assemble a new carrying cartridge on the shaft for subsequent uses thereby improving convenience for the user in use.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims and their equivalents.

What is claimed is:

1. A rotation module, for being disposed in a housing of a test device, comprising:
   a rotation body, comprising:
      a shaft, pivoted in the housing;
      a position limiting element, telescoped on the shaft;
      a reciprocation element, telescoped on the shaft, wherein the reciprocation element has a groove; and
      a rotation element, engaged with the shaft, wherein the rotation element is located between the position limiting element and the reciprocation element, and the position limiting element, the rotation element and the reciprocation element are disposed along the shaft; and
   a driving element, slideably disposed in the housing and coupled to the groove, when the driving element moves back and forth towards a first direction and an opposite direction of the first direction, the driving element driving the reciprocation element to rotate back and forth relative to the position limiting element through the groove, and the rotation element being pushed by the reciprocation element to rotate along a rotation direction relative to the position limiting element for driving the shaft to rotate along the rotation direction.

2. The rotation module of claim 1, wherein the rotation element has a first engaging portion and a second engaging portion opposite to each other, the position limiting element has a third engaging portion, and the reciprocation element has a fourth engaging portion, wherein the first engaging portion of the rotation element engages with the fourth engaging portion of the reciprocation element, and the second engaging portion of the rotation element engages with the third engaging portion of the position limiting element.

3. The rotation module of claim 2, wherein when the driving element moves towards the first direction, the fourth engaging portion of the reciprocation element pushes the first engaging portion of the rotation element for driving the rotation element to rotate along the rotation direction, and the second engaging portion of the rotation element slides relative to the third engaging portion of the position limiting element.

4. The rotation module of claim 2, wherein the position limiting element is slideably disposed on the housing, and the rotation body further comprises:
   an elastic element, telescoped on the shaft and leaning against the housing and the position limiting element for providing a pre-stress to hold the engagement between the second engaging portion of the rotation element and the third engaging portion of the position limiting element.

5. The rotation module of claim 2, wherein when the driving element moves towards the opposite direction of the first direction, the fourth engaging portion of the reciprocation element slides relative to the first engaging portion of the rotation element, and the third engaging portion of the position limiting element blocks the second engaging portion of the rotation element for limiting the rotation element from rotating along an opposite direction of the rotation direction.

6. The rotation module of claim 2, wherein the first engaging portion of the rotation element comprises at least one first elastic locking hook, and the second engaging portion of the rotation element comprises at least one second elastic locking hook, wherein the first engaging portion of the rotation element engages with the fourth engaging portion of the reciprocation element through the first elastic locking hook, and the second engaging portion of the rotation element engages with the third engaging portion of the position limiting element through the second elastic locking hook.

7. A test device, comprising:
   a housing;
   a rotation module, disposed in the housing, wherein the rotation module comprises:
      a rotation body, comprising:
         a shaft, pivoted in the housing;
         a position limiting element, telescoped on the shaft;
         a reciprocation element, telescoped on the shaft, and the reciprocation element having a groove; and
         a rotation element, engaged with the shaft, and the rotation element being located between the position limiting element and the reciprocation element, and the position limiting element, the rotation element and the reciprocation element are disposed along the shaft; and
      a driving element, slideably disposed in the housing and coupled to the groove; and
   a carrying cartridge, detachably disposed on the shaft, wherein the carrying cartridge has a plurality of perforated grooves; and
   a push rod, connected to the driving element, and the push rod being aligned to any one of the perforated grooves,
   wherein when the driving element moves back and forth towards a first direction and an opposite direction of the first direction, the driving element drives the reciprocation element to rotate back and forth relative to the position limiting element through the groove, and the rotation element is pushed by the reciprocation element to rotate along a rotation direction relative to the position limiting element for driving the shaft to rotate along the rotation direction and driving the carrying cartridge to rotate along the rotation direction together with the shaft, and the push rod is aligned to a next one of the perforated grooves.

8. The test device of claim 7, wherein the rotation element has a first engaging portion and a second engaging portion opposite to each other, the position limiting element has a third engaging portion, and the reciprocation element has a fourth engaging portion, wherein the first engaging portion of the rotation element engages with the fourth engaging portion of the reciprocation element, and the second engaging portion of the rotation element engages with the third engaging portion of the position limiting element.

9. The test device of claim 8, wherein when the driving element moves towards the first direction, the fourth engaging portion of the reciprocation element pushes the first engaging portion of the rotation element for driving the rotation element to rotate along the rotation direction, and the second engaging portion of the rotation element slides relative to the third engaging portion of the position limiting element.

10. The test device of claim 8, wherein the position limiting element is slideably disposed on the housing, and the rotation body further comprises:
    an elastic element, telescoped on the shaft and leaning against the housing and the position limiting element for providing a pre-stress to hold the engagement between the second engaging portion of the rotation element and the third engaging portion of the position limiting element.

11. The test device of claim 8, wherein when the driving element moves towards the opposite direction of the first direction, the fourth engaging portion of the reciprocation element slides relative to the first engaging portion of the rotation element, and the third engaging portion of the position limiting element blocks the second engaging portion of the rotation element for limiting the rotation element from rotating along an opposite direction of the rotation direction.

12. The test device of claim 8, wherein the first engaging portion of the rotation element comprises at least one first elastic locking hook, and the second engaging portion of the rotation element comprises at least one second elastic locking hook, wherein the first engaging portion of the rotation element engages with the fourth engaging portion of the reciprocation element through the first elastic locking hook, and the second engaging portion of the rotation element engages with the third engaging portion of the position limiting element through the second elastic locking hook.

13. The test device of claim 7, wherein the carrying cartridge comprises a plurality of consumables sideably disposed in the perforated grooves, and when the driving element moves towards the first direction, the driving element drives the push rod to move into the next one of the perforated grooves being aligned and moves the consumable inside the next one of perforated grooves out of the carrying cartridge.

14. A test device, comprising:
a housing;
a rotation body, comprising:
  a shaft, pivoted in the housing;
  a position limiting element, telescoped on the shaft and non-rotatably disposed in the housing;
  a reciprocation element, telescoped on the shaft, and the reciprocation element having a groove; and
  a rotation element, engaged with the shaft, wherein the position limiting element, the rotation element and the reciprocation element are disposed along the shaft, wherein the rotation element engages with the reciprocation element through a first ratchet wheel structure, and the rotation element engages with the position limiting element through a second ratchet wheel structure, and the rotation element is limited to unidirectionally rotate by the first ratchet wheel structure and the second ratchet wheel structure;
a driving element, slideably disposed in the housing and coupled to the groove;
a carrying cartridge, detachably disposed on the shaft, wherein the carrying cartridge has a plurality of perforated grooves; and
a push rod, connected to the driving element;
wherein when the driving element moves back and forth along a direction, the driving element drives the reciprocation element to move back and forth through the groove for driving the rotation element to unidirectionally rotate while driving the shaft and the carrying cartridge to unidirectionally rotate.

15. The test device of claim 14, wherein when the driving element moves back and forth along the direction, the push rod is moved together with the driving element along the same direction.

\* \* \* \* \*